(12) United States Patent
Schrader et al.

(10) Patent No.: US 9,510,744 B2
(45) Date of Patent: Dec. 6, 2016

(54) ENDOSCOPE

(75) Inventors: Stephan Schrader, Kleinmachnow (DE); Stefan Oginski, Berlin (DE); Daniel Brueggemann, Berlin (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 386 days.

(21) Appl. No.: 13/158,139

(22) Filed: Jun. 10, 2011

(65) Prior Publication Data

US 2011/0306834 A1 Dec. 15, 2011

(30) Foreign Application Priority Data

Jun. 11, 2010 (DE) .................... 10 2010 024 003

(51) Int. Cl.

| | |
|---|---|
| *A61B 1/00* | (2006.01) |
| *A61B 1/04* | (2006.01) |
| *A61B 1/06* | (2006.01) |
| *A61B 1/12* | (2006.01) |
| *G02B 23/24* | (2006.01) |
| *F28D 15/04* | (2006.01) |
| *F28D 21/00* | (2006.01) |

(52) U.S. Cl.
CPC ............. *A61B 1/12* (2013.01); *A61B 1/00066* (2013.01); *A61B 1/00121* (2013.01); *A61B 1/0676* (2013.01); *A61B 1/0684* (2013.01); *A61B 1/128* (2013.01); *G02B 23/2476* (2013.01); *G02B 23/2484* (2013.01); *F28D 15/04* (2013.01); *F28D 2021/005* (2013.01)

(58) Field of Classification Search
CPC ... A61B 1/0676; A61B 1/0684; A61B 1/128

USPC ........ 600/101, 109–113, 127–130, 160–182; 348/45, 65–74; 356/241.1–241.6
See application file for complete search history.

(56) References Cited

U.S. PATENT DOCUMENTS

| | | | |
|---|---|---|---|
| 7,914,448 B2 | 3/2011 | Bob et al. | |
| 2005/0158687 A1* | 7/2005 | Dahm | 433/29 |

(Continued)

FOREIGN PATENT DOCUMENTS

| | | |
|---|---|---|
| DE | 29613103 U1 | 10/1997 |
| DE | 102009049196 A1 | 5/2010 |
| EP | 1731862 A1 | 12/2006 |
| EP | 1738679 A2 | 1/2007 |

(Continued)

OTHER PUBLICATIONS

European Search Report; Application No. EP 11 16 9262; Issued: Aug. 29, 2011; Mailing Date: Sep. 5, 2011; 8 pages.

*Primary Examiner* — Ryan Henderson
(74) *Attorney, Agent, or Firm* — Whitmyer IP Group LLC

(57) ABSTRACT

An endoscope comprises an elongated shaft, a headpiece at a proximal end of the shaft, the headpiece having a housing, at least one light source which is arranged in the shaft in a distal area thereof, and produces lost heat, and a passive cooling which has at least one heat pipe which is arranged in the shaft and is thermally coupled to the at least one light source in order to lead away the lost heat in the proximal direction. The at least one heat pipe extends into the headpiece, and a heat sink body is arranged in the headpiece, to which heat sink body the at least one heat pipe is thermally coupled, and which absorbs the lost heat from the at least one heat pipe and emits the lost heat to the environment directly or via the housing of the headpiece.

49 Claims, 7 Drawing Sheets

(56) References Cited

U.S. PATENT DOCUMENTS

| | | |
|---|---|---|
| 2006/0183977 A1* | 8/2006 | Ishigami ............ A61B 1/00177 600/179 |
| 2006/0268552 A1 | 11/2006 | Irion et al. |
| 2008/0151046 A1 | 6/2008 | Scott et al. |
| 2008/0208006 A1 | 8/2008 | Farr |
| 2008/0208297 A1 | 8/2008 | Gertner et al. |
| 2010/0003633 A1 | 1/2010 | Senn et al. |
| 2010/0087712 A1* | 4/2010 | Ito ................................ 600/160 |
| 2011/0092772 A1 | 4/2011 | Weber et al. |

FOREIGN PATENT DOCUMENTS

| | | | |
|---|---|---|---|
| EP | 2311366 A1 | 4/2011 | |
| JP | 11299775 A * | 11/1999 | ............... A61B 8/00 |
| JP | 2007007321 A | 1/2007 | |
| JP | 2007007322 A | 1/2007 | |
| JP | 2007229261 A | 9/2007 | |
| JP | 2009011612 A * | 1/2009 | ............... A61B 1/00 |
| JP | 2009247620 A * | 10/2009 | ............... A61B 1/00 |
| WO | 2004011848 A2 | 2/2004 | |

* cited by examiner

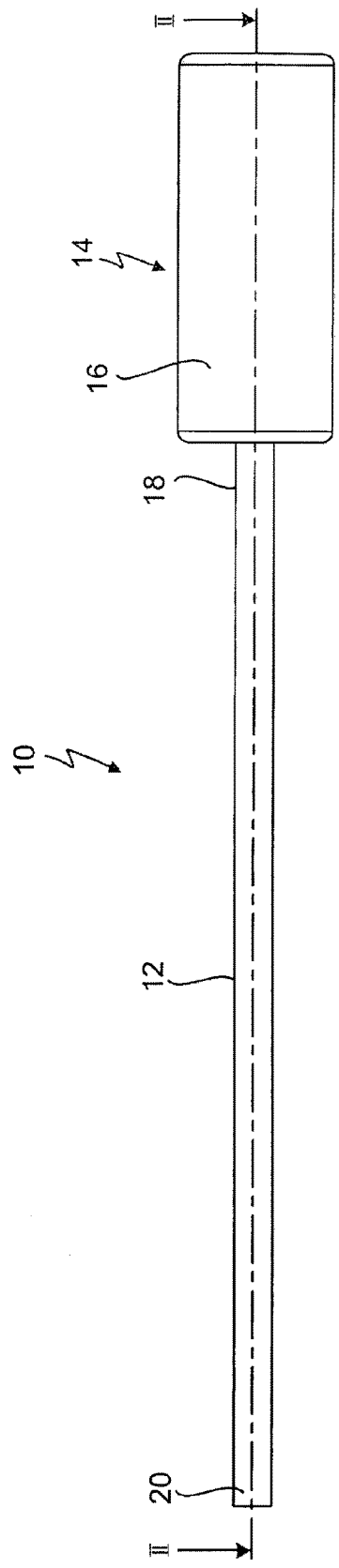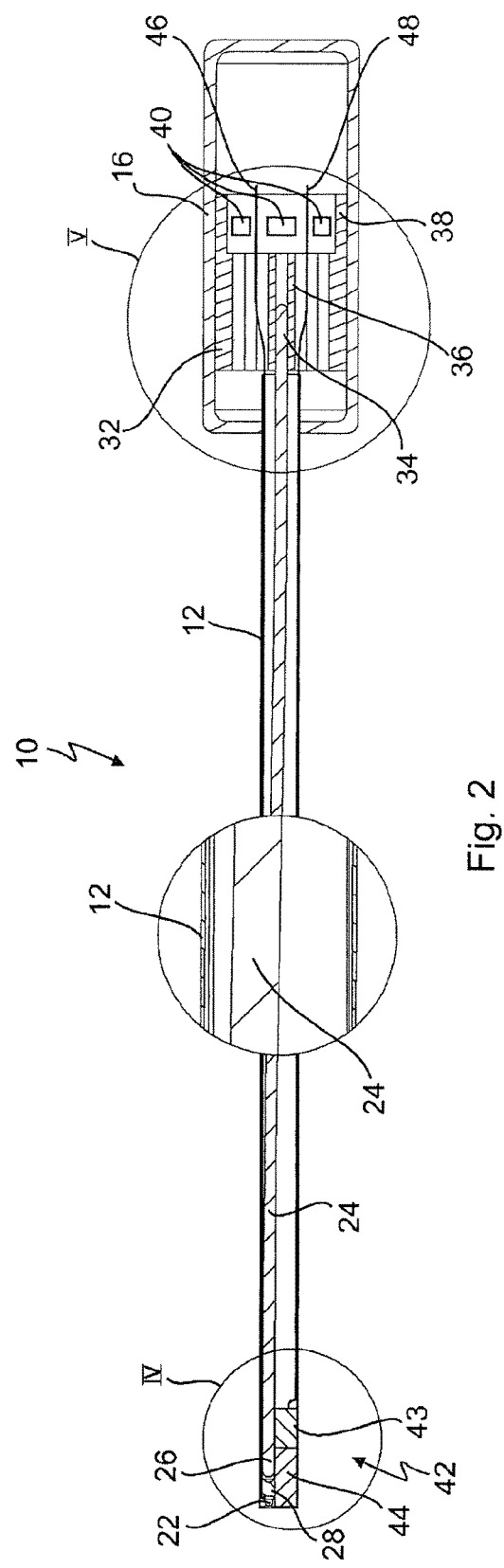

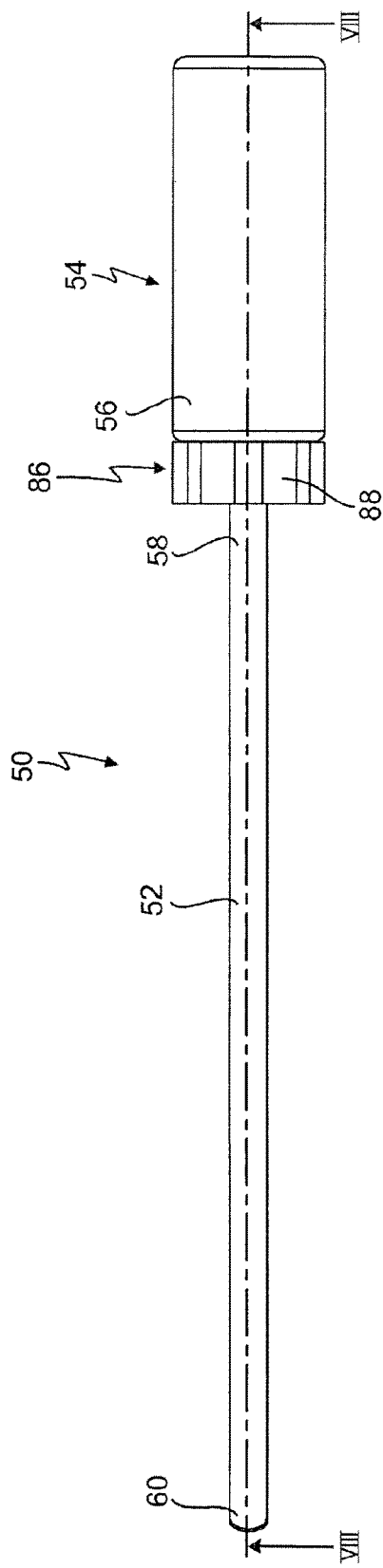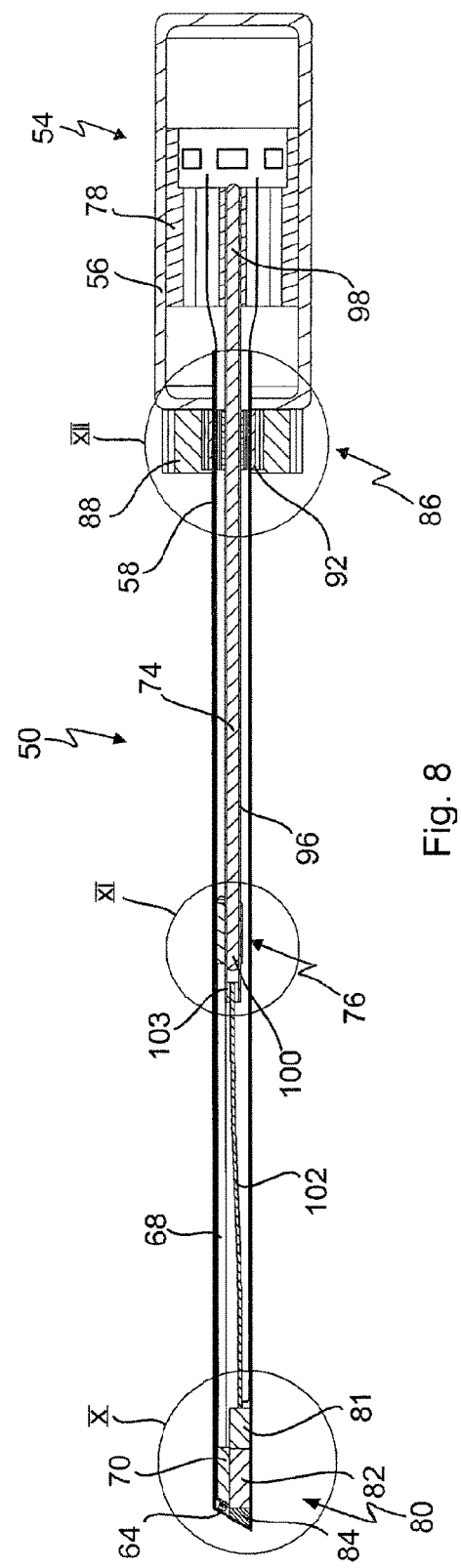
Fig. 7
Fig. 8

ENDOSCOPE

CROSS REFERENCE TO RELATED APPLICATION

This application claims priority from German patent application 102010024003.6, filed on Jun. 11, 2010. The entire contents of these priority application is incorporated herein by reference.

BACKGROUND OF THE INVENTION

The invention relates to an endoscope having at least one light source and a passive cooling in order to lead away lost heat produced by the light source, in proximal direction.

The present invention relates in particular to a medical endoscope, which is used as a viewing instrument during minimal invasive surgery. In the case of a medical endoscope such as this, the elongated shaft is partially inserted into the body through an artificially created or natural opening.

Nowadays, endoscopes have one or more light sources which are integrated in the endoscope shaft and are in the form of light-emitting diodes (LEDs). The integration of one or more light sources in the shaft of the endoscope, normally in the distal area of the shaft, means that there is no need for any external light source, for example a xenon lamp. The advantage of one or more light sources which are integrated in the shaft of the endoscope is that there is no need for an optical waveguide which is required when using an external light source, thus improving the ergonomics of the endoscope. The lack of external light sources and optical waveguides also reduces the production and procurement costs of endoscopes.

However, an endoscope which has a light source integrated in the shaft is subject to the technical problem that the light source produces lost heat in its vicinity in the shaft during operation, which also heats the shaft severely, in particular in the area of the distal end of the shaft, where the light source or sources is or are arranged.

An endoscope which is used for surgery is subject to the regulations of medical product law. According to the medical product law, the outside of the endoscope shaft must not exceed a temperature of 41° C., in order to prevent heat-dependent damage being caused to tissue in the human or animal body.

However, modern high-power LEDs produce lost heat which is so great that the shaft would quickly rise above the required maximum temperature of 41° C. Against this background, it is necessary to provide cooling in the shaft, to lead away lost heat such that the shaft is not heated above the legally stipulated maximum temperature.

Various concepts are known for cooling or leading away the lost heat.

In the case of an endoscope that is known from US 2008/0151046 A1, which is an endoscope for industrial purposes for examining machines, in particular aircraft engines, a heat pipe whose distal end is thermally conductively coupled to the light source is provided for leading away the lost heat from the light source which is arranged in the distal area of the shaft and is in the form of an LED. A heat pipe such as this is a heat transmitter which uses the heat of vaporization of a substance which is contained in the heat pipe to allow a high heat flow density, that is to say large amounts of heat can be transported in a small cross-sectional area. No additional auxiliary power, such as a circulation pump, is required to circulate the substance which is provided as the heat transport medium in the heat pipe, thus minimizing the maintenance effort and operating costs of a heat pipe such as this.

In a heat pipe, the heat carrier medium is vaporized at the "warm" end of the heat pipe, with the vapour being passed to the "cold" end, where the vapour condenses again. Latent heat is therefore used for leading away heat, as a result of which the thermal conduction in a heat pipe is many times greater than the thermal conduction in, for example, copper. In the heat pipe, liquid which is used as the heat transport medium is fed back by means of capillaries to the vaporization end on the basis of the wicking principle. The condensed fluid therefore flows back to the vaporization end of the heat pipe in the capillary independently of the orientation, that is to say to that end of the heat pipe which is coupled to the light source. As a result of the use of the capillary principle, heat pipes therefore operate in any desired orientations with respect to the force of gravity.

In the case of the known endoscope mentioned above, the heat pipe extends proximally over a short length of the shaft of the endoscope, and a thermally conductive wire, for example a copper wire, is connected to the proximal end of the heat pipe, with the wire extending further proximally, and with its proximal end being thermally conductively connected to the inside of the shaft of the endoscope.

However, this type of cooling is insufficient for a medical endoscope, because the heat is transmitted from the heat pipe to the shaft of the endoscope, as a result of which the shaft is heated, what, however, is intended to be avoided in a medical endoscope.

DE 296 13 103 U1 discloses an endoscope for medical purposes, in the distal end of whose shaft light-emitting elements are arranged, with channels being provided in the shaft in order to pass a fluid through, for cooling.

JP 2007 007 321 A discloses an endoscope in the distal area of whose shaft a light source, which is in the form of an LED, is arranged, with a pipeline being laid in the shaft, for cooling or for leading away the lost heat from the LED, through which pipeline air is passed for cooling.

Further endoscopes, in which the cooling for the light source arranged in the shaft is provided by means of an external cooling circuit are known from JP 2007 229 261 A, JP 2007 007 322 and EP 1 738 679 A2.

In the known cooling concepts mentioned above, the endoscope shaft is therefore cooled by means of an external cooling circuit, with a cooling medium, for example a gaseous or liquid cooling medium, being passed through the shaft.

However, the disadvantage of a cooling concept such as this is that external cooling lines, circulation pumps and a reservoir for the cooling medium are required, for example, for the cooling circuit, which on the one hand increases the production effort and cost of an endoscope such as this, and on the other hand also adversely affects the ergonomics of the endoscope, because the endoscope must be connected to external cooling lines of the cooling circuit, which have a disturbing effect when the endoscope is being handled during a surgical procedure.

SUMMARY OF THE INVENTION

It is, therefore, an object of the present invention to improve an endoscope of the type mentioned initially such that the lost heat is led away reliably from the at least one light source that is arranged in the shaft of the endoscope, with little production effort and cost.

According to an aspect of the invention, an endoscope is provided, comprising an elongated shaft having a distal end, a distal area and a proximal end, a headpiece arranged at the proximal end of the shaft, the headpiece having a housing, at least one light source arranged in the shaft in the distal area thereof and producing lost heat, a passive cooling, the passive cooling having at least one heat pipe arranged in the shaft and being thermally coupled to the at least one light source in order to lead away the lost heat in proximal direction, the at least one heat pipe extending into the headpiece, a heat sink body arranged in the headpiece and thermally coupled to the at least one heat pipe, the heat sink body absorbing the lost heat from the at least one heat pipe and emitting the lost heat to the environment.

The endoscope according to the invention therefore exploits the advantages of a heat pipe for leading away of the lost heat produced by the at least one light source in the distal area of the shaft, thus avoiding a cooling circuit, and therefore connections for supplying a cooling medium and connections for leading away the cooling medium, and external cooling lines. Since the at least one heat pipe extends into the headpiece in which a heat sink body is arranged, the lost heat is transported at a high transmission rate to the headpiece, where the heat is emitted to the large-area housing of the headpiece, that is to say to a large area and, via this or directly, to the environment. In the latter case, the heat sink body may itself be a part of the housing of the headpiece. Since, in the case of a medical endoscope, the headpiece is arranged outside the human or animal body during a surgical procedure, leading away the heat via the headpiece to the environment does not lead to damage caused by heat to tissue within the human or animal body. In the case of the endoscope according to the invention, the shaft of the endoscope is therefore adequately protected against heating, as a result of which the endoscope according to the invention meets the legal requirements for the maximum temperature of the shaft. The headpiece, which has a larger area than the endoscope shaft, is well able to absorb the heat from the heat body, which likewise has a large area, and to emit it to the environment. The design of the endoscope according to the invention with a heat pipe for leading away the lost heat produced by the at least one light source results overall in the capability to produce the endoscope at very low cost and in a simple design form, as a result of which the endoscope according to the invention is also suitable for use as a disposable endoscope.

In one preferred refinement, at least in the area of its distal end, the shaft is thermally insulated on the inside from the at least one heat pipe.

Since the heat pipe is itself heated by the lost heat absorbed from the at least one light source and this heat is admittedly led away proximally, the measure mentioned above advantageously avoids the heat pipe from emitting heat to the shaft and the shaft being heated above the maximum permissible temperature in this way.

In this refinement, the insulation can be implemented by providing insulation on the outside of the heat pipe, for example a heat-insulating coating, and/or by providing insulation on the inside of the shaft, that is to say by providing a heat-insulating coating on the inner wall of the shaft, and/or by arranging a heat-insulating tube between the shaft inner wall and the outer wall of the at least one heat pipe.

In a further preferred refinement, electronic and/or electrical components are arranged in a cavity in the heat sink body.

In this case, it is advantageous that the heat sink body in the headpiece of the endoscope emits not only the heat emitted from the heat pipe to the headpiece, but also the lost heat which is produced by the electronic or electrical components. Electronic or electrical components such as these are provided in the endoscope in particular if the endoscope is a video endoscope with a camera in the distal area of the shaft or in the headpiece.

In a further preferred refinement, a distal end of the at least one heat pipe is thermally conductively connected to the at least one light source by means of a heat coupling element.

In comparison to thermal coupling of the at least one light source to the at least one heat pipe via thermal radiation, this measure has the advantage that the heat transmission from the at least one light source to the at least one heat pipe is further improved by thermal conduction. In this case, a heat coupling element may be a solid body whose material has high thermal conductivity, for example copper or aluminium. The heat coupling element in this case preferably makes contact over as large an area as possible with the at least one light source and the at least one heat pipe without there being any air gaps in these touching areas, and this can be achieved by soldering, adhesive bonding or the like.

In a further preferred refinement, the heat sink body surrounds a proximal end area of the at least one heat pipe, and makes direct contact with it.

As when heat is transmitted from the at least one light source to the at least one heat pipe by means of the heat coupling element mentioned above, this measure results in the abovementioned advantages of very good heat transmission, even from the proximal end area of the at least one heat pipe to the heat sink body.

In a further preferred refinement, the at least one heat pipe comprises a first heat pipe which is coupled to the at least one light source and extends to an intermediate area in the shaft between the distal and proximal ends thereof, and at least one second heat pipe which is thermally coupled to the first heat pipe, which second heat pipe extends from the intermediate area into the headpiece, and is thermally coupled to the heat sink body.

This measure on the one hand has the advantage that it is also possible to provide endoscopes with very long shafts with the cooling concept according to the invention via a cascade of heat pipes. On the other hand, this measure has the advantage that endoscopes with semi-flexible shafts can also be equipped with the cooling concept according to the invention, by a plurality of heat pipes, each having only a shorter length than the shaft and being connected one behind the other to form a non-rigid arrangement.

In this context, it is also preferable for the first heat pipe and the at least one second heat pipe to partially overlap in the intermediate area in the longitudinal direction of the shaft.

This measure advantageously contributes to improved heat transmission between the individual heat pipes, and therefore to leading away the lost heat into the headpiece of the endoscope in an improved manner.

In a further preferred refinement, the first heat pipe and the at least one second heat pipe are thermally conductively connected to one another in the intermediate area by means of a heat coupling element which surrounds the first and the at least one second heat pipe.

This measure improves the heat transmission in the heat transport direction even further, particularly if, as already indicated in a comparable refinement above, the heat coupling element is composed of a material which is very highly thermally conductive, for example of copper or aluminium.

In the refinements mentioned above, the "cold" end of the respective distal side heat pipe emits the lost heat to the "warm" end of the respectively following heat pipe, which then transports the heat losses further proximally.

In a further preferred refinement of the measures mentioned above, the heat coupling element is flexible.

In this case, it is advantageous for the cascade arrangement of the individual heat pipes to be "articulated", while at the same time providing very good heat transmission between the individual heat pipes, as a result of which this refinement is particularly suitable for endoscopes with semi-flexible shafts. A flexible heat coupling element such as this may, for example, be in the form of one or more flexible wires which, for example, are manufactured from copper.

In yet another preferred refinement of the measures mentioned above, the at least one second heat pipe can rotate relative to the shaft about a longitudinal axis of the at least one second heat pipe, the at least one second heat pipe being connected on the one hand to a camera, which is arranged in the distal area of the shaft, and on the other hand to a rotating drive, in order to allow the camera to rotate relative to the shaft about its own optical axis.

In this refinement, the endoscope is a video endoscope which has a camera arranged in the distal area of the shaft. Particularly in the case of video endoscopes having so-called oblique viewing optics, in which the viewing direction through the endoscope is directed obliquely with respect to the longitudinal axis of the shaft of the endoscope, provision is normally made for the capability to rotate the shaft and the camera relative to one another. The background to this relative rotation capability is that the shaft is rotated about its own longitudinal axis in order to change the viewing direction. In order not to rotate the horizon of the image recorded by the camera in this case, because the medical practitioner using the endoscope could otherwise lose his orientation in the observation area, the camera can therefore rotate relative to the shaft, in such a way that the perceived image can always be kept upright by relative rotation of the camera with respect to the shaft. By way of example, the camera has an image sensor and an objective arranged in front of it. Where the present application states that the camera can rotate or is rotated, this also means that only the image sensor can rotate or is rotated relative to the shaft, while the objective is fixed to the shaft, or that both the image sensor and the objective can rotate or are rotated relative to the shaft.

In the measure mentioned above, the at least one second heat pipe therefore advantageously has two functions, specifically on the one hand to lead away the lost heat from the at least one light source proximally, and on the other hand the transmission of the torque from the rotating drive to the camera. Further parts for the rotating drive for the camera are advantageously saved in this way, thus saving costs and production effort.

In this context, it is also preferable if the rotating drive has a magnetic coupling, which has a driving actuating element, which is arranged externally on the shaft, and a driven element, which interacts magnetically with the actuating element and is arranged in the shaft, and to which the at least one second heat pipe is coupled in rotationally fixed manner relative to one another.

If the rotating drive is arranged at the distal end of the headpiece, the at least one second heat pipe is preferably passed through the driven element, such that the proximal end of the at least one second heat pipe engages in the heat sink body. The driven element is in this case preferably a magnetically acting ring, to which the at least one second heat pipe is coupled in rotationally fixed manner to one another. The distal end of the at least one second heat pipe is in this case preferably coupled to the camera via a spindle, in particular a flexible spindle, in rotationally fixed manner relative to one another.

In conjunction with one of the abovementioned refinements, according to which the first heat pipe and the at least one second heat pipe are thermally conductively connected to one another in the intermediate area by means of a heat coupling element, a further preferred refinement provides that the at least one second heat pipe can rotate relative to the heat coupling element.

Since the at least one light source is normally arranged in the distal area of the shaft in rotationally fixed manner relative to the shaft, and the first heat pipe correspondingly as well, the measure mentioned above results in a refinement of simple design, by means of which the at least one second heat pipe can on the one hand transmit a torque from the rotating drive to the camera, while on the other hand the heat coupling element ensures a good thermally conductive connection between the first heat pipe and the at least one second heat pipe. The heat coupling element is therefore used as a rotating bearing for the at least one second heat pipe, in which case air gaps can be avoided by means of an appropriate heat coupling medium (for example a gel) in order to ensure good heat transmission from the heat coupling element to the at least one second heat pipe. The second heat pipe is likewise arranged such that it can rotate relative to the heat sink body, for example by being mounted in it such that it can rotate, while the heat sink body is arranged in the headpiece in rotationally fixed manner.

In a further preferred refinement, at least two heat pipes are thermally coupled to the at least one light source.

In this embodiment, the heat dissipation from the at least one light source is further improved by the provision of at least two heat pipes, which are coupled to the at least one light source. The at least two heat pipes may in this case extend from the at least one light source to the heat sink body in the headpiece, or the individual heat pipes extend from the at least one light source into an intermediate area of the shaft, where they are then thermally coupled to the at least one second heat pipe, while only the second heat pipe extends to the heat sink body in the headpiece. The latter refinement is once again particularly suitable for an at least semi-flexible configuration of the shaft of the endoscope, and in particular also for a video endoscope having a camera which can rotate.

The refinement mentioned above also covers the situation in which two or more light sources are arranged in the distal area of the shaft of the endoscope, and a total of two or more heat pipes are thermally coupled to these light sources, in which case it is self-evident that the number of light sources need not correspond to the number of heat pipes. It is therefore possible for the endoscope to have two or more light sources and only one heat pipe, or only one light source and two or more heat pipes, which is or are thermally coupled to the light source or to the light sources.

In conjunction with the refinement described above, it is also preferable for the at least two heat pipes to be jointly thermally coupled via the heat coupling element to the at least one light source.

In this case, it is advantageous to provide only one heat coupling element for coupling the heat pipes to the light source or light sources, thus advantageously reducing the number of parts of the cooling system, and the production effort for the endoscope.

Further features and advantages will become evident from the following description and the attached drawing.

It is self-evident that the features mentioned above and those which are still to be explained in the following text can be used not only in the respectively stated combination but also in other combinations or on their own without departing from the scope of the present invention.

BRIEF DESCRIPTION OF THE DRAWINGS

Exemplary embodiments of the invention are illustrated in the drawing and will be described in more detail in the following text with reference thereto. In the drawings:

FIG. 1 shows a side view of a first exemplary embodiment of an endoscope;

FIG. 2 shows a longitudinal section through the endoscope shown in FIG. 1, along a line II-II in FIG. 1, illustrating a shaft of the endoscope, partially enlarged;

FIG. 7 shows a side view of a further exemplary embodiment of an endoscope;

FIG. 8 shows a longitudinal section through the endoscope along the line VIII-VIII in FIG. 7;

DETAILED DESCRIPTION OF EXEMPLARY PREFERRED EMBODIMENTS

Figure 3:
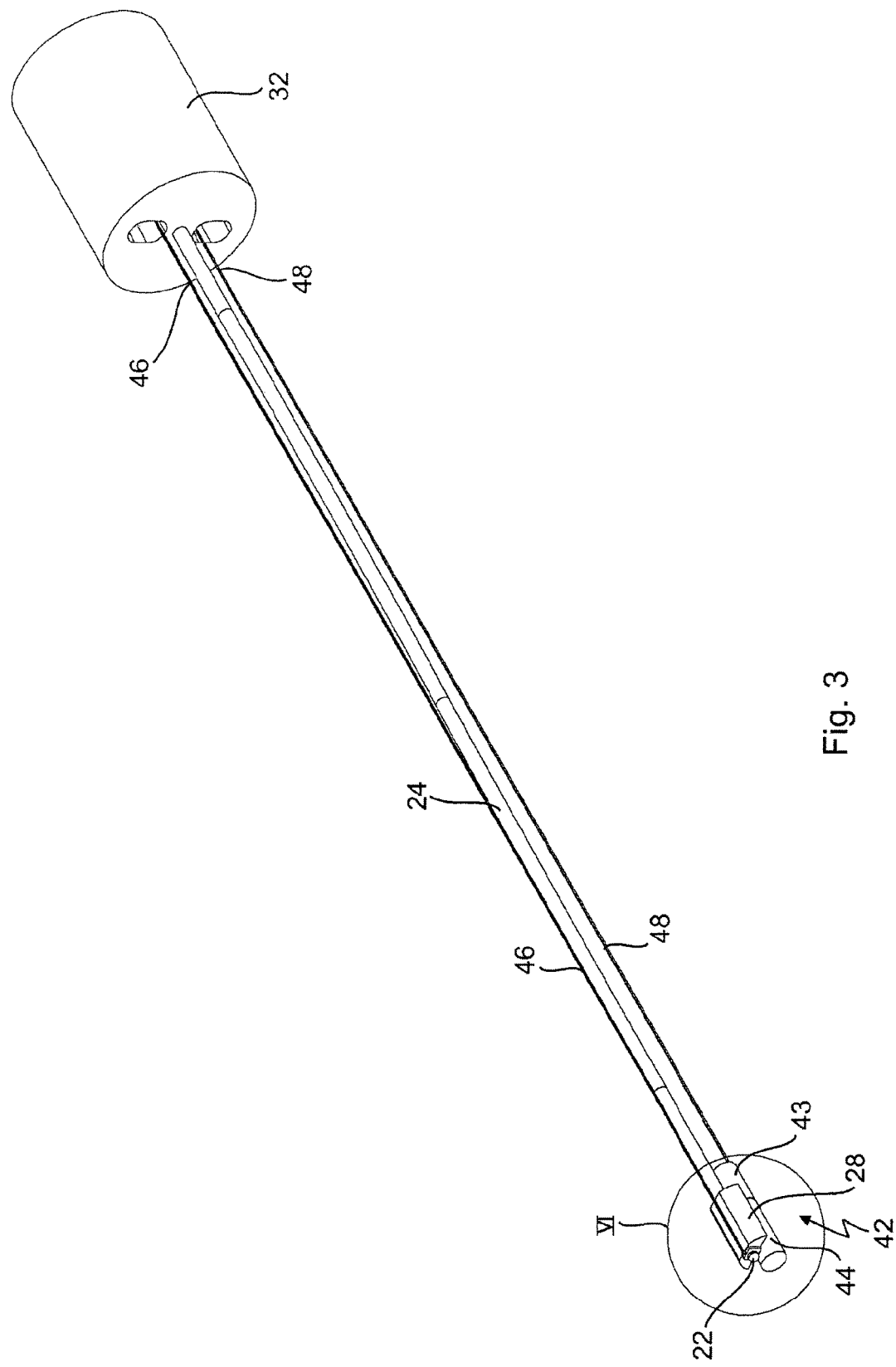
FIG. 3 shows a perspective illustration of the endoscope in FIG. 1, without a shaft and without a housing of a headpiece.

FIG. 1 shows an endoscope, in particular a medical video endoscope, which is provided with the general reference symbol 10.

FIGS. 2 to 6 illustrate further details of the endoscope 10, to which reference will likewise be made in the following text.

The endoscope 10 generally has an elongated shaft 12 and a headpiece 14 with a housing 16 at a proximal end 18 of the shaft 12. A distal end of the shaft 12 is provided with the reference symbol 20 in FIG. 1.

Figure 4:
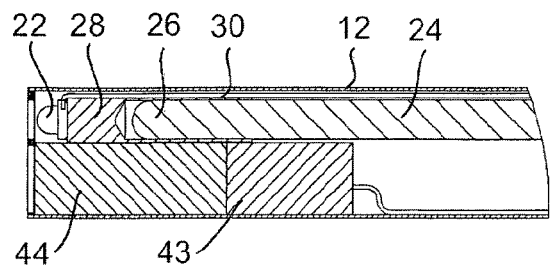
FIG. 4 shows an enlarged illustration of the detail IV in FIG. 2.
Figure 6:
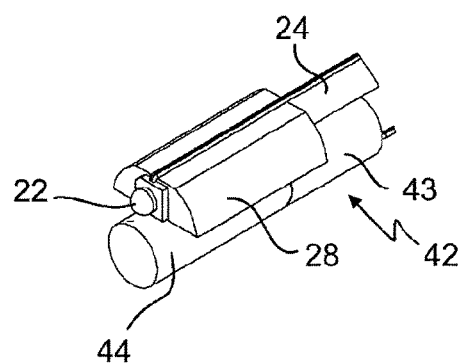
FIG. 6 shows an enlarged illustration of the detail VI in FIG. 3.
Figure 9:
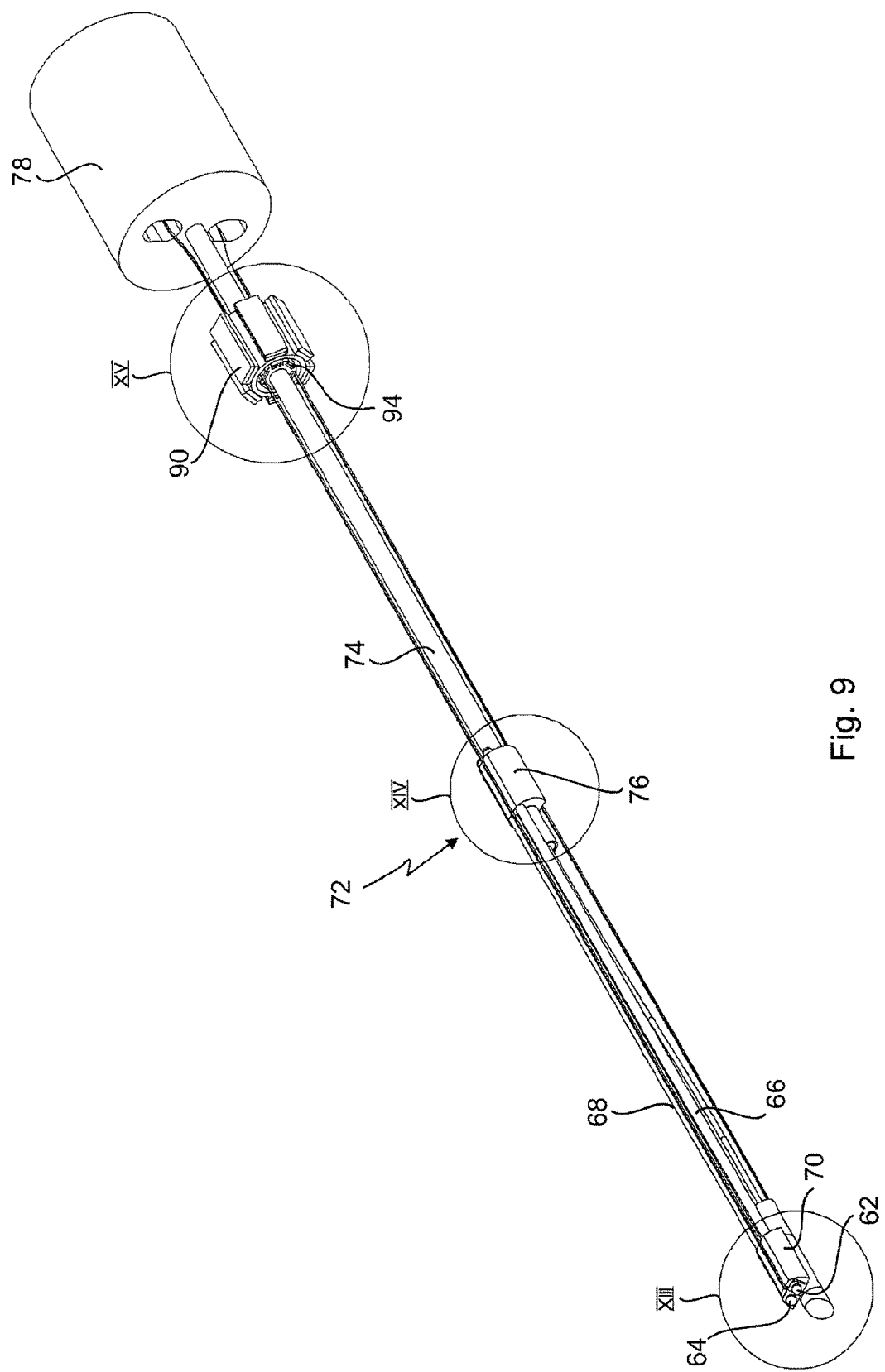
FIG. 9 shows a perspective illustration of the endoscope in FIG. 7, without a shaft and without a housing of a headpiece.
Figure 10:
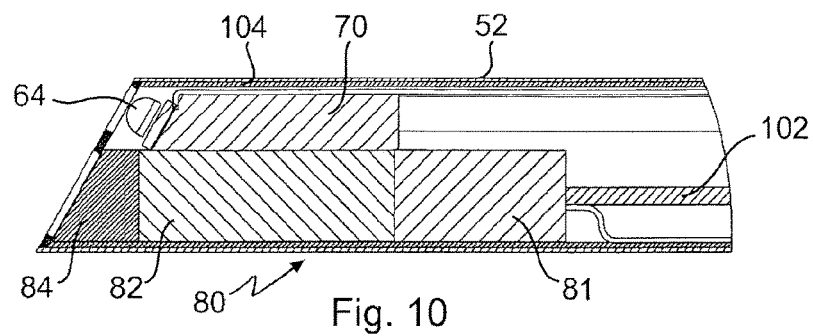
FIG. 10 shows an enlarged illustration of the detail X in FIG. 8.
Figure 11:
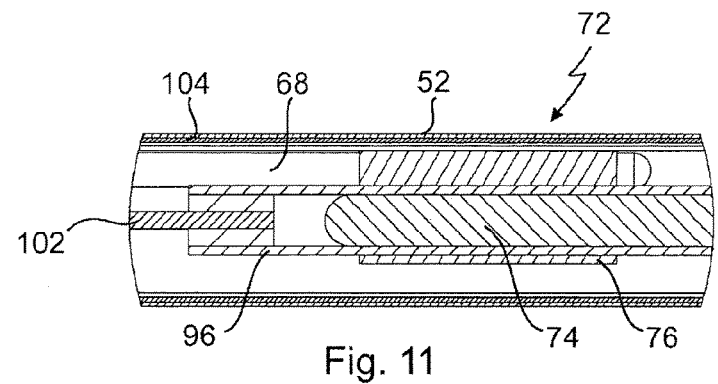
FIG. 11 shows an enlarged illustration of the detail XI in FIG. 8.

A light source 22 is arranged in a distal area of the shaft 12 which is shown on its own in particular in FIGS. 4 and 6, and the light source 22 is preferably in the form of a high-power light-emitting diode (LED or OLED). The light source 22 produces lost heat during operation.

In order to lead away the lost heat from the light source 22, in order to prevent the shaft 12 from being heated above the maximum permissible temperature of 41° C. in accordance with the medical product law, particularly in the area of its distal end 20, the endoscope 10 has a passive cooling, which has a heat pipe 24 arranged in the shaft 12.

The heat pipe 24 has a distal end 26, which is thermally coupled to the light source 22. The thermal coupling is provided via a heat coupling element 28, which is manufactured as a solid body composed of a highly thermally conductive material, for example copper or aluminium.

The heat coupling element 28 has an extension 30 in the form of a sleeve, as is illustrated in FIG. 4, which receives the distal end 26 of the heat pipe 24 without an air gap, in order to ensure that heat is transmitted particularly well from the heat coupling element 28 to the heat pipe 24. The heat coupling element 28 is itself thermally conductively connected over an area to the rear face of the light source 22.

Figure 5:
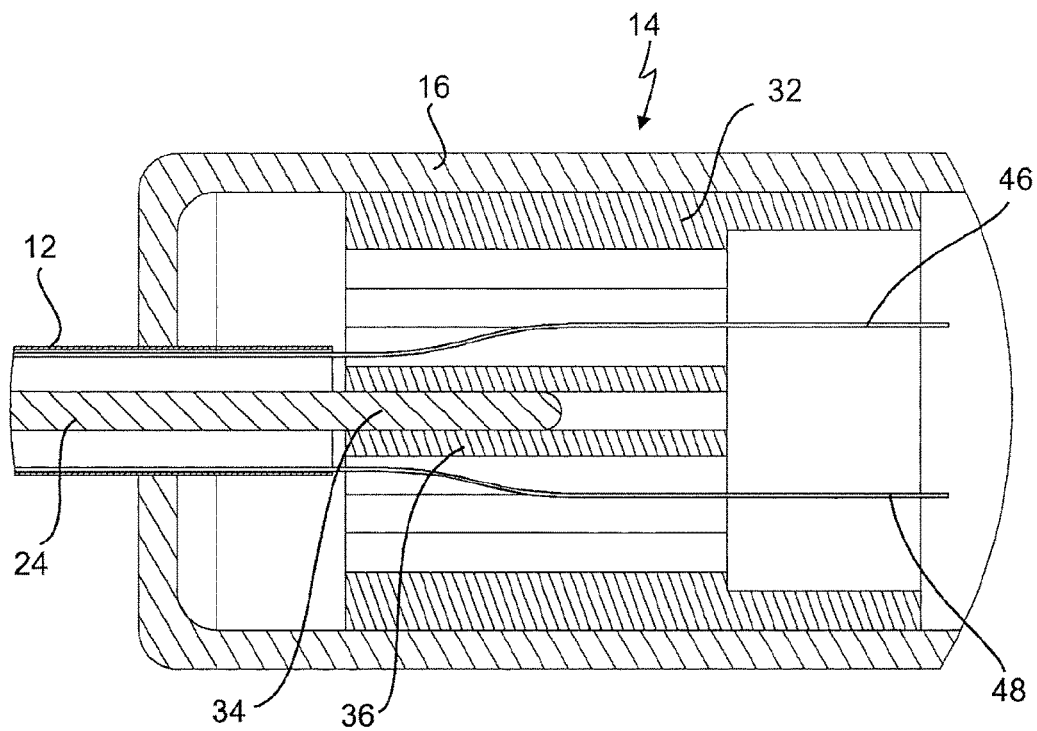
FIG. 5 shows an enlarged illustration of the detail V in FIG. 2.

As is shown in FIG. 2, the heat pipe 24 extends through the shaft 12 into the headpiece 14, that is to say it projects into the housing 16 of the headpiece 14. As is shown in FIGS. 2, 3 and 5, a heat sink body 32 is arranged in the headpiece 14, and the heat pipe 24 is thermally coupled to it. For this purpose, a proximal end 34 of the heat pipe 24 is thermally conductively connected to the heat sink body 32 in an inner sleeve 36 of the heat sink body 32. The heat sink body 32 is itself thermally conductively connected over an area to the housing 16, such that the heat sink body 32 can transmit the heat absorbed from the heat pipe 24 to the housing 16 of the headpiece 14, and the heat is then emitted to the environment from the headpiece 14. The heat sink body 32 is tubular or in the form of a rod, and has an external circumference with a large area, with the headpiece 14 likewise having a large area. The external diameter of the heat sink body 32 and the external diameter of the housing 16 of the headpiece are greater than the external diameter of the shaft 12. The heat sink body 32 may also itself be part of the housing 16, and can then emit the absorbed heat directly to the environment.

When the endoscope 10 is being used in a surgical procedure, the headpiece 14 is located outside the human or animal body, as a result of which the heat emitted via the headpiece 14 causes no damage to the environment. In contrast, the outside of the shaft 12 remains below the maximum permissible temperature, at least in the area which is inserted into the human or animal body during the surgical procedure.

Furthermore, electronic and/or electrical components 40 are arranged in a cavity, which is formed by a sleeve-like extension 38, in the heat sink body 32, and their lost heat is likewise transmitted from the heat sink body 32 to the housing 16.

Furthermore, at least in the area of the distal end 20, preferably as far as the headpiece 14, the heat pipe 24 is thermally isolated from the inner face of the shaft 12. This can be achieved by insulating sheathing of the heat pipe 24 itself or by insulation on the inner face of the shaft 12, as will also be described later with reference to a further exemplary embodiment.

The endoscope 10 furthermore has a camera 42 which, for example, has a CCD or CMOS-based image sensor 43, which is arranged in the distal area of the shaft 12. An objective 44 is arranged on the light entrance side in front of the image sensor 43.

An electrical line 46 is provided for the light source 22, and an electrical line 48 is provided for the image sensor 43, and these electrical lines extend from the light source 22 and from the image sensor 43, respectively, into the headpiece 14, as is illustrated in FIGS. 2 and 5. The electrical lines 46 and 48 lead to corresponding electrical connections (not illustrated) at the proximal end of the headpiece 14.

As already mentioned above, there is a heat pipe 24 provided. Accordingly, there are capillaries and a heat carrier medium in the heat pipe 24, with the heat carrier medium being vaporized by the lost heat absorbed from the light source 22 at the distal end, and being condensed again at the proximal end 34 of the heat pipe 24, from where the heat carrier medium passes back again to the distal end by virtue of the capillary effect. The heat carrier medium therefore stores heat in the form of latent heat, which is transported proximally, where it is emitted again in the form of latent heat. The heat transmission capability of a heat pipe is many times greater than the heat transport capability of, for example, a copper wire.

A further exemplary embodiment of an endoscope, which is provided with the general reference symbol 50, will be described in the following text with reference to FIGS. 7 to 15. In particular, the endoscope 50 is a medical video endoscope.

In general, the endoscope 50 has a shaft 52 and a headpiece 54 with a housing 56. The headpiece 54 is arranged at a proximal end 58 of the shaft 52. A distal end of the shaft 52 is provided with the reference symbol 60.

A first light source 62 and a second light source 64 are arranged in the distal area of the shaft 52. The light sources 62 and 64 are in the form of LEDs or OLEDs. The light sources 62 and 64 produce lost heat during operation, as has already been described in conjunction with the previous exemplary embodiment. In order to lead away the lost heat and in order to avoid heating of the shaft 52 above the permissible extent, the endoscope 50 has a first heat pipe 66, which is thermally coupled to the light sources 62 and 64, and a further heat pipe 68, which is thermally coupled to the light sources 62 and 64. A heat coupling element 70 is provided for the thermal coupling between the heat pipes 66 and 68 and the light sources 62 and 64, into which the distal ends of the heat pipes 66 and 68 are inserted, as far as possible without any air gap, from the proximal side, with the heat coupling element 70 itself being thermally conductively connected to the light sources 62 and 64. In this case, the heat coupling element 70 is once again in the form of a solid body, which is manufactured from a highly thermally conductive material, for example copper or aluminium.

The first heat pipe 66 and the further heat pipe 68 extend into an intermediate area 72 (cf. FIGS. 8, 9 and 11), which is located between the distal end 60 and the proximal end 58 of the shaft 52. In this case, there is no need for the intermediate area 72 to be located in the centre between the distal end 60 and the proximal end 58, and, instead, it can also be arranged at points other than those illustrated.

In the intermediate area 72, the first heat pipe 66 and the further heat pipe 68 are thermally coupled to a second heat pipe 74. A further heat coupling element 76 is arranged in the intermediate area 72 for this purpose and is thermally conductively connected both to the proximal ends of the first heat pipe 66 and of the heat pipe 68, and to the distal end of the second heat pipe 74. In this case, the heat coupling element 76 surrounds the proximal ends of the heat pipes 66 and 68 on the one hand, and the distal end of the second heat pipe 74, on the other hand. This once again ensures good heat transmission from the heat pipes 66 and 68 to the second heat pipe 74.

In this case, the heat coupling element 76 can itself be designed to be flexible, such that the arrangement, in the form of a cascade, consisting of the heat pipes 66, 68 on the one hand and the second heat pipe 74 on the other hand is articulated to a certain extent in the intermediate area 72, thus allowing the shaft 52 of the endoscope 50 also to be designed, in particular, to be semi-flexible.

The second heat pipe 74 now extends into the headpiece 54, in which it is thermally coupled to a heat sink body 78, in which case reference is made with respect to the thermal coupling and the configuration of the heat sink body 78 to the description of the heat sink body 32 in the previous exemplary embodiment, and electronic and/or electrical components can once again be arranged in the heat sink body 78 in this case.

The endoscope 50 furthermore has a camera 80, which is arranged in the distal area of the shaft 52 and has, for example, a CCD or CMOS version of an image sensor 81. On the distal side of the image sensor 81, the camera 80 has an objective 82. Furthermore, the objective 82 has oblique viewing optics 84, thus allowing the viewing direction of the endoscope 50 to include an angle other than 0°, for example a 30° angle, with the longitudinal axis of the shaft 52. The oblique viewing optics 84 may also be integrated in the objective 82.

With the same orientation of the longitudinal axis of the shaft 52, rotation of the shaft 52 about its longitudinal axis allows the endoscope 50 to look in different viewing directions in the observed area. In order to simplify the orientation on the video monitor (not illustrate) on which the endoscope image is visually displayed, for the medical practitioner who is using the endoscope, provision is made in the endoscope 50 for the camera 80, in this case only the image sensor 81 of the camera 80, to have the capability to rotate about the optical axis of the camera 80 relative to the shaft 52.

A rotating drive 86, which is in the form of a magnetic coupling, is correspondingly provided for the camera 80 (image sensor 81) on the headpiece 54.

The rotating drive 86 has a driving actuating element 88, which is arranged externally on the shaft 52 at the proximal end 58, and is in the form of a hand wheel. The actuating element 88 has a plurality of magnets 90 on its inner circumference. The magnetic poles are illustrated by N and S in FIG. 12.

Figure 12:
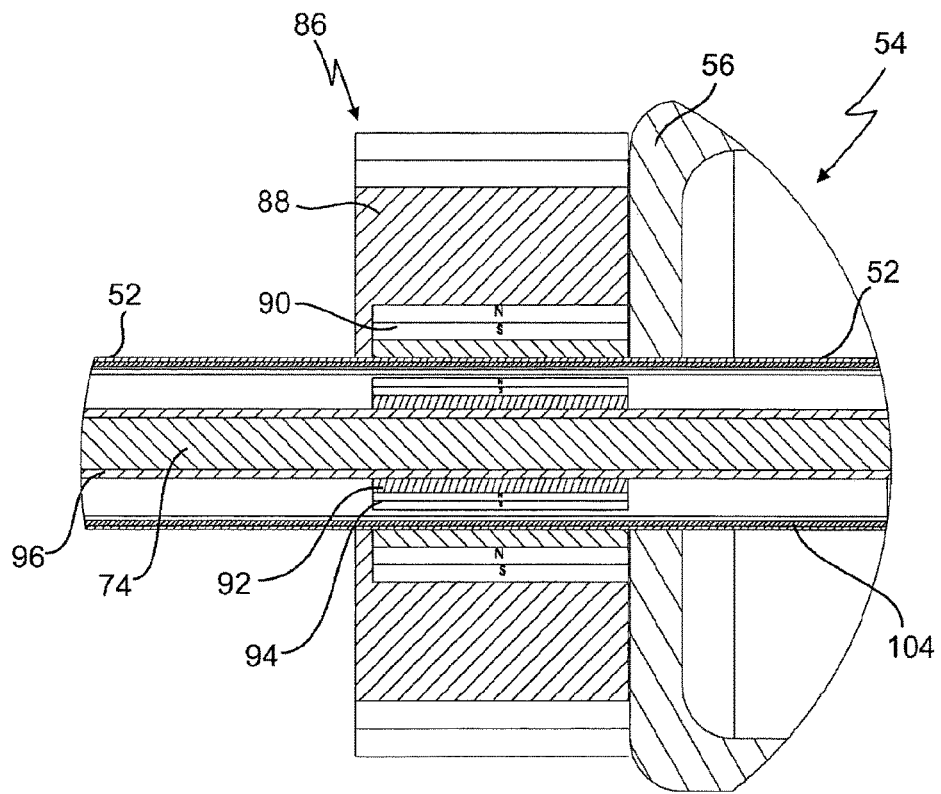
FIG. 12 shows an enlarged illustration of the detail XII in FIG. 8.
Figure 13:
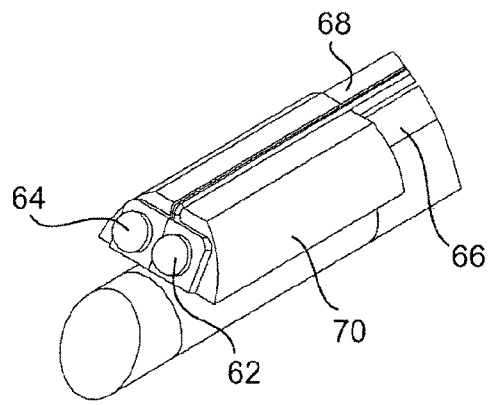
FIG. 13 shows an enlarged illustration of the detail XIII in FIG. 9.
Figure 14:
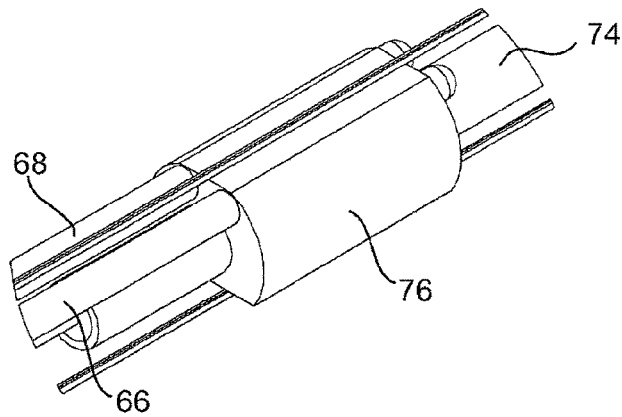
FIG. 14 shows an enlarged illustration of the detail XIV in FIG. 9.
Figure 15:
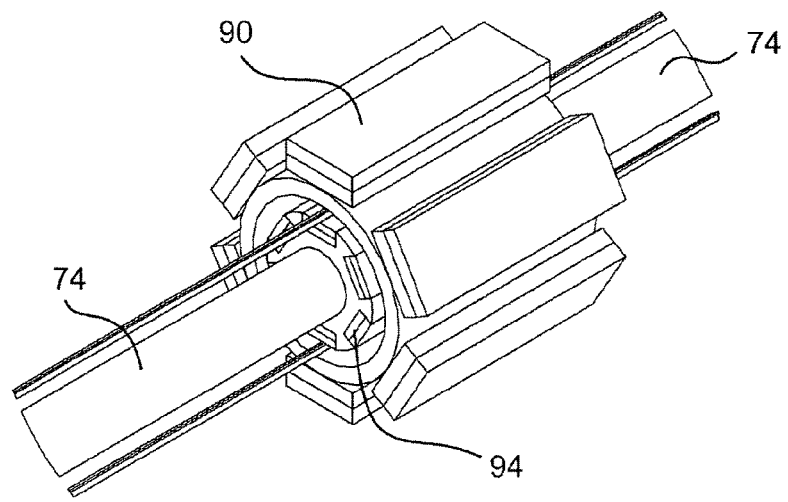
FIG. 15 shows an enlarged illustration of the detail XV in FIG. 9.

The rotating drive 86 furthermore has a driven element 92 which interacts magnetically with the actuating element 88 and likewise has a plurality of magnets 94 (cf. FIG. 9), whose poles are likewise illustrated by N and S in FIG. 12. Because of the magnetic force link between the magnets 90 on the actuating element 88 and the magnet 94 on the driven element 92, the driven element 92 follows a rotational movement of the actuating element 88 in the same rotation direction.

In this case, the second heat pipe 74 is coupled to the driven element 92, passing through it, in rotationally fixed manner so that rotation of the driven element 92 about its longitudinal axis results in the second heat pipe 74 being rotated in the same rotation direction. The second heat pipe 74 is likewise received in the shaft such that it can rotate about its longitudinal axis relative to the shaft 52. In this exemplary embodiment, the second heat pipe 74 is therefore used not only for heat transport of the lost heat from the light sources 62 and 64 into the headpiece 54, but also as a torque transmission element for the camera 80.

In order to provide better protection for the heat pipe 74 against mechanical loads when torque is being transmitted, the second heat pipe 74 is surrounded by a tube 96 which, for example, is manufactured from copper or aluminium, or in general from a thermally highly conductive material.

The second heat pipe 74 is mounted such that it can rotate in the intermediate area 72 in the heat coupling element 76, while the heat coupling element 76 is itself held such that it cannot rotate, in the same way as the first heat pipe 66 and the second heat pipe 68, as well as the light sources 62 and 64.

In this case, the rotatable bearing of the second heat pipe 74 in the heat coupling element 76 is realized such that a good heat transmission from the heat pipes 66 and 68 to the second heat pipe 74 is ensured.

A proximal end 98 of the second heat pipe 74 is likewise mounted in the headpiece 54 such that it can rotate in the heat sink body 78.

A torque transmission element 102 extends distally from a distal end 100 of the second heat pipe 74 and is in this case in the form of a flexible spindle, which is particularly advantageous when the rotation axis of the camera 80 is not aligned with the longitudinal axis of the second heat pipe 74, as is illustrated in particular in FIG. 8.

In this case, the torque transmission element 102 is coupled to a distal end 103 of the tube 96 in rotationally fixed manner relative to one another.

In order to vary the viewing direction of the endoscope 50, the shaft 52 is rotated about its longitudinal axis, and in order not to change the orientation of the camera 80, the actuating element 88 is held fixedly, as a result of which the second heat pipe 74 is likewise held fixedly via the driven element 92 and the camera 80 is held fixedly via the torque transmission element 102, thus preventing the camera 80 from rotating about its own optical axis, as a result of which the shaft 52 rotates about the camera 80.

As in the previous exemplary embodiment, the shaft 52 is thermally isolated from the heat pipes 66, 68 and 74. For this purpose, the shaft 52 is provided on the inside with thermal insulation 104, which is in the form of an intermediate tube composed of a thermally insulated material. The thermal insulation 104 in this case extends from the distal end of the shaft 52 to the proximal end of the shaft, part of which projects into the headpiece 54, as is illustrated in FIGS. 8 and 12.

Alternatively or additionally, the heat pipes 66, 68 and 74 may also be sheathed with thermal insulation (not shown) on the outside.

It is self-evident that, in the case of the exemplary embodiment shown in FIGS. 7 to 15, it is also possible to provide only one light source, for example the light source 64, in which case only the heat pipe 68 is then thermally coupled to the second heat pipe 74 in the intermediate area 72, while the rest of the configuration, in particular the capability of the second heat pipe 74 to rotate relative to the shaft 52, is maintained.

Conversely, the endoscope 50 may also have more than the two light sources 62 and 64 and a greater number of heat pipes 66, 68, in which case, however, a total of two heat pipes 66, 68 is advantageous for two light sources 62 and 64, because the shaft 52 may possibly have a very small diameter.

Furthermore, the heat pipe cascade comprising the first heat pipe 66, the further heat pipe 68 and the second heat pipe 74 may also be formed in three, four etc., stages, rather than the two stages as in the present case.

What is claimed is:

1. An endoscope, comprising:
   an elongated shaft having a distal end, a distal area and a proximal end,
   a headpiece arranged at the proximal end of the shaft, the headpiece having a housing,
   at least one light source arranged in the shaft in the distal area thereof and producing lost heat,
   a passive cooling, the passive cooling having:
   at least one heat pipe arranged in the shaft and being thermally coupled to the at least one light source in order to lead away the lost heat in proximal direction, the at least one heat pipe extending into the headpiece,
   a heat sink body arranged in the headpiece and thermally coupled to the at least one heat pipe, the heat sink body absorbing the lost heat from the at least one heat pipe and emitting the lost heat to an environment of said headpiece,
   wherein the at least one heat pipe comprises a first heat pipe coupled to the at least one light source and extending to an intermediate area in the shaft between the distal and proximal ends thereof, and at least one second heat pipe thermally coupled to the first heat pipe, the second heat pipe extending from the intermediate area into the headpiece, and being thermally coupled to the heat sink body, and
   a camera arranged in the distal area of the shaft, and a rotating drive, wherein the at least one second heat pipe is rotatable relative to the shaft about a longitudinal axis of the at least one second heat pipe, the at least one second heat pipe being connected to the camera, and to the rotating drive, in order to allow the camera to rotate relative to the shaft about an optical axis of the camera, wherein the camera is connected to the at least one second heat pipe via a torque transmission member.

2. The endoscope of claim 1, wherein, at least in the distal area, the shaft is internally thermally insulated from the at least one heat pipe.

3. The endoscope of claim 1, wherein electronic and/or electrical components are arranged in a cavity in the heat sink body.

4. The endoscope of claim 1, further comprising a heat coupling element thermally conductively coupling a distal end of the at least one heat pipe to the at least one light source.

5. The endoscope of claim 1, wherein the heat sink body surrounds a proximal end area of the at least one heat pipe, and makes direct contact with it.

6. The endoscope of claim 1, wherein the first heat pipe and the at least one second heat pipe partially overlap with one another in the intermediate area in longitudinal direction of the shaft.

7. The endoscope of claim 1, further comprising a heat coupling element thermally conductively connecting the first heat pipe and the at least one second heat pipe to one another in the intermediate area, the heat coupling element surrounding the first and the at least one second heat pipe.

8. The endoscope of claim 7, wherein the heat coupling element is flexible.

9. The endoscope of claim 1, wherein the rotating drive comprises a magnetic coupling, which has a driving actuating element, which is arranged externally on the shaft, and a driven element, which interacts magnetically with the actuating element and is arranged in the shaft, and to which the at least one second heat pipe is coupled in rotationally fixed manner.

10. The endoscope of claim 7, wherein the at least one second heat pipe is rotatable relative to the heat coupling element.

11. The endoscope of claim 1, wherein the passive cooling comprises at least two heat pipes thermally coupled to the at least one light source.

12. The endoscope of claim 11, wherein the at least two heat pipes are jointly thermally coupled via a heat coupling element to the at least one light source.

13. The endoscope of claim 11, wherein the at least two heat pipes comprise a first heat pipe and at least one further heat pipe, the first heat pipe and the at least one further heat pipe being coupled to the at least one light source and extending to an intermediate area in the shaft between the distal and proximal ends thereof, and the passive cooling further comprises at least one second heat pipe thermally coupled to the first heat pipe and the at least one further heat pipe in the intermediate area, the at least one second heat pipe extending from the intermediate area into the headpiece and being thermally coupled to the heat sink body.

14. An endoscope, comprising:
an elongated shaft having a distal end, a distal area and a proximal end,
a headpiece arranged at the proximal end of the shaft, the headpiece having a housing,
at least one light source arranged in the shaft in the distal area thereof and producing lost heat,
a passive cooling, the passive cooling having:
at least one heat pipe arranged in the shaft and being thermally coupled to the at least one light source in order to lead away the lost heat in proximal direction, the at least one heat pipe extending into the headpiece,
a heat sink body arranged in the headpiece and thermally coupled to the at least one heat pipe, the heat sink body absorbing the lost heat from the at least one heat pipe and emitting the lost heat to an environment of said headpiece,
wherein, at least in the distal area, the shaft is internally thermally insulated from the at least one heat pipe,
wherein the at least one heat pipe comprises a first heat pipe coupled to the at least one light source and extending to an intermediate area in the shaft between the distal and proximal ends thereof, and at least one second heat pipe thermally coupled to the first heat pipe, the second heat pipe extending from the intermediate area into the headpiece, and being thermally coupled to the heat sink body,
further comprising a camera arranged in the distal area of the shaft, and a rotating drive, wherein the at least one second heat pipe is rotatable relative to the shaft about a longitudinal axis of the at least one second heat pipe, the at least one second heat pipe being connected to the camera, and to the rotating drive, in order to allow the camera to rotate relative to the shaft about an optical axis of the camera, wherein the camera is connected to the at least one second heat pipe via a torque transmission member.

15. The endoscope of claim 14, wherein electronic and/or electrical components are arranged in a cavity in the heat sink body.

16. The endoscope of claim 14, further comprising a heat coupling element thermally conductively coupling a distal end of the at least one heat pipe to the at least one light source.

17. The endoscope of claim 14, wherein the heat sink body surrounds a proximal end area of the at least one heat pipe, and makes direct contact with it.

18. The endoscope of claim 14, wherein the first heat pipe and the at least one second heat pipe partially overlap with one another in the intermediate area in longitudinal direction of the shaft.

19. The endoscope of claim 14, further comprising a heat coupling element thermally conductively connecting the first heat pipe and the at least one second heat pipe to one another in the intermediate area, the heat coupling element surrounding the first and the at least one second heat pipe.

20. The endoscope of claim 19, wherein the heat coupling element is flexible.

21. The endoscope of claim 14, wherein the rotating drive comprises a magnetic coupling, which has a driving actuating element, which is arranged externally on the shaft, and a driven element, which interacts magnetically with the actuating element and is arranged in the shaft, and to which the at least one second heat pipe is coupled in rotationally fixed manner.

22. The endoscope of claim 19, wherein the at least one second heat pipe is rotatable relative to the heat coupling element.

23. The endoscope of claim 14, wherein the passive cooling comprises at least two heat pipes thermally coupled to the at least one light source.

24. The endoscope of claim 23, wherein the at least two heat pipes are jointly thermally coupled via a heat coupling element to the at least one light source.

25. The endoscope of claim 23, wherein the at least two heat pipes comprise a first heat pipe and at least one further heat pipe, the first heat pipe and the at least one further heat pipe being coupled to the at least one light source and extending to an intermediate area in the shaft between the distal and proximal ends thereof, and the passive cooling further comprises at least one second heat pipe thermally coupled to the first heat pipe and the at least one further heat pipe in the intermediate area, the at least one second heat pipe extending from the intermediate area into the headpiece and being thermally coupled to the heat sink body.

26. An endoscope, comprising:
an elongated shaft having a distal end, a distal area and a proximal end,
a headpiece arranged at the proximal end of the shaft, the headpiece having a housing,
at least one light source arranged in the shaft in the distal area thereof and producing lost heat,
a passive cooling, the passive cooling having:
at least one heat pipe arranged in the shaft and being thermally coupled to the at least one light source in order to lead away the lost heat in proximal direction, the at least one heat pipe extending into the headpiece,
a heat sink body arranged in the headpiece and thermally coupled to the at least one heat pipe, the heat sink body absorbing the lost heat from the at least one heat pipe and emitting the lost heat to an environment of said headpiece,
wherein the at least one heat pipe comprises a first heat pipe having a first distal end coupled to the at least one light source and a first proximal end terminating at an intermediate area in the shaft between the distal and proximal ends thereof, and at least one second heat pipe having a second distal end thermally coupled to the first proximal end of the first heat pipe, the second heat pipe extending from the intermediate area into the headpiece, and having a second proximal end being thermally coupled to the heat sink body, wherein the heat sink body surrounds a proximal end area of the at least one heat pipe, and makes direct contact with it, further comprising a heat coupling element thermally conductively connecting the first heat pipe and the at least one second heat pipe to one another in the intermediate area, the heat coupling element surrounding the first and the at least one second heat pipe.

27. The endoscope of claim 26, wherein, at least in the distal area, the shaft is internally thermally insulated from the at least one heat pipe.

28. The endoscope of claim 26, wherein electronic and/or electrical components are arranged in a cavity in the heat sink body.

29. The endoscope of claim 26, further comprising a heat coupling element thermally conductively coupling a distal end of the at least one heat pipe to the at least one light source.

30. The endoscope of claim 26, wherein the first heat pipe and the at least one second heat pipe partially overlap with one another in the intermediate area in longitudinal direction of the shaft.

31. The endoscope of claim 26, wherein the heat coupling element is flexible.

32. The endoscope of 26, further comprising a camera arranged in the distal area of the shaft, and a rotating drive, wherein the at least one second heat pipe is rotatable relative to the shaft about a longitudinal axis of the at least one second heat pipe, the at least one second heat pipe being connected to the camera, and to the rotating drive, in order to allow the camera to rotate relative to the shaft about an optical axis of the camera, wherein the camera is connected to the at least one second heat pipe via a torque transmission member.

33. The endoscope of claim 31, wherein the rotating drive comprises a magnetic coupling, which has a driving actuating element, which is arranged externally on the shaft, and a driven element, which interacts magnetically with the actuating element and is arranged in the shaft, and to which the at least one second heat pipe is coupled in rotationally fixed manner.

34. The endoscope of claim 26, wherein the at least one second heat pipe is rotatable relative to the heat coupling element.

35. The endoscope of claim 26, wherein the passive cooling comprises at least two heat pipes thermally coupled to the at least one light source.

36. The endoscope of claim 35, wherein the at least two heat pipes are jointly thermally coupled via a heat coupling element to the at least one light source.

37. An endoscope, comprising:
an elongated shaft having a distal end, a distal area and a proximal end,
a headpiece arranged at the proximal end of the shaft, the headpiece having a housing,
at least one light source arranged in the shaft in the distal area thereof and producing lost heat,
a passive cooling, the passive cooling having:
at least one heat pipe arranged in the shaft and being thermally coupled to the at least one light source in order to lead away the lost heat in proximal direction, the at least one heat pipe extending into the headpiece,
a heat sink body arranged in the headpiece and thermally coupled to the at least one heat pipe, the heat sink body absorbing the lost heat from the at least one heat pipe and emitting the lost heat to an environment of said headpiece, wherein the passive cooling comprises at least two heat pipes thermally coupled to the at least one light source, wherein the at least two heat pipes comprise a first heat pipe having a first distal end and at least one further heat pipe, the first heat pipe and the at least one further heat pipe being coupled to the at least one light source and a first proximal end of the first heat pipe terminating at an intermediate area in the shaft between the distal and proximal ends thereof, and the passive cooling further comprises at least one second heat pipe having a second distal end thermally coupled to the first proximal end of the first heat pipe and the at least one further heat pipe in the intermediate area, the at least one second heat pipe extending from the intermediate area into the headpiece and having a second proximal end being thermally coupled to the heat sink body.

38. The endoscope of claim 37, wherein, at least in the distal area, the shaft is internally thermally insulated from the at least two heat pipes.

39. The endoscope of claim 37, wherein electronic and/or electrical components are arranged in a cavity in the heat sink body.

40. The endoscope of claim 37, further comprising a heat coupling element thermally conductively coupling a distal end of the at least two heat pipes to the at least one light source.

41. The endoscope of claim 37, wherein the heat sink body surrounds a proximal end area of the at least two heat pipes, and makes direct contact with it.

42. The endoscope of claim 37, wherein the first heat pipe and the at least one second heat pipe partially overlap with one another in the intermediate area in longitudinal direction of the shaft.

43. The endoscope of claim 37, further comprising a heat coupling element thermally conductively connecting the first heat pipe and the at least one second heat pipe to one another in the intermediate area, the heat coupling element surrounding the first and the at least one second heat pipe.

44. The endoscope of claim 43, wherein the heat coupling element is flexible.

45. The endoscope of claim 37, further comprising a camera arranged in the distal area of the shaft, and a rotating drive, wherein the at least one second heat pipe is rotatable relative to the shaft about a longitudinal axis of the at least one second heat pipe, the at least one second heat pipe being connected to the camera, and to the rotating drive, in order to allow the camera to rotate relative to the shaft about an optical axis of the camera, wherein the camera is connected to the at least one second heat pipe via a torque transmission member.

46. The endoscope of claim 45, wherein the rotating drive comprises a magnetic coupling, which has a driving actuating element, which is arranged externally on the shaft, and a driven element, which interacts magnetically with the actuating element and is arranged in the shaft, and to which the at least one second heat pipe is coupled in rotationally fixed manner.

47. The endoscope of claim 43, wherein the at least one second heat pipe is rotatable relative to the heat coupling element.

48. The endoscope of claim 37, wherein the at least two heat pipes are jointly thermally coupled via a heat coupling element to the at least one light source.

49. The endoscope of claim 37, wherein a third proximal end of the at least one further heat pipe terminates at the intermediate area, and at least one second heat pipe having a second distal end further thermally coupled to the third proximal end in the intermediate area.

\* \* \* \* \*